United States Patent [19]

Miki et al.

[11] Patent Number: 5,112,602
[45] Date of Patent: May 12, 1992

[54] DEODORANT CARRYING URETHANE FOAM AND PROCESS OF PREPARING THE SAME

[75] Inventors: Yoshiaki Miki; Tsunehisa Ueda, both of Kanagawa; Nobuaki Hiramatsu; Koji Toyonaka, both of Tokyo, all of Japan

[73] Assignee: Nippon Zeon Co., Ltd., Tokyo, Japan

[21] Appl. No.: 184,124

[22] Filed: Apr. 20, 1988

[30] Foreign Application Priority Data

Apr. 23, 1987 [JP]  Japan .................................. 62-98535

[51] Int. Cl.⁵ .............................................. A61L 9/04
[52] U.S. Cl. .................................. 424/76.3; 424/76.2
[58] Field of Search ...................... 424/76.3, 76.7, 76.2

[56] References Cited

U.S. PATENT DOCUMENTS 4,469,848  9/1984  Hooper .............................. 424/76.9

FOREIGN PATENT DOCUMENTS

| 53-0698 | 6/1978 | Japan | 424/76.3 |
| 60-1451 | 7/1985 | Japan . | |
| 61-2458 | 1/1986 | Japan | 424/76.3 |
| 61-2130 | 9/1986 | Japan | 424/76.3 |
| 61-2556 | 11/1986 | Japan | 424/76.7 |
| 62-1425 | 6/1987 | Japan | 424/76.8 |

*Primary Examiner*—Thurman K. Page
*Attorney, Agent, or Firm*—Lowe, Price, Leblanc & Becker

[57] ABSTRACT

A deodorant carrying urethane foam contains a chemically-reactive deodorant distributed uniformly therein wherein weight loss of said deodorant is not more than 15% when kept at atmospheric pressure and 150° C. for 1 hr. The process of preparing the above-mentioned deodorant carrying urethane foam comprises adding a chemically-reactive deodorant to a urethane foam composition with mixing to permit said deodorant to be uniformly distributed therein, and then causing the resultant mixture to react and produce a foam.

10 Claims, No Drawings

DEODORANT CARRYING URETHANE FOAM AND PROCESS OF PREPARING THE SAME

BACKGROUND OF THE INVENTION

1. Field of the Invention

The present invention relates to a deodorant carrying urethane foam for use in removing undesirable odors as from air in a room, or the like.

2. Description of the Prior Art

So far a number of deodorants are found in the form of liquid and powder, and these may be sprayed or spread as they are, and also are used frequently in combination with other material, for instance, in the form impregnated into or carried by a suitable material. In particular, urethane foam is characterized by good processability, large surface structure and also by air-permeability if the cellular structure has through-foams, and thus adequate for combined use with deodorant.

Under the circumstances, for example, are presented a deodorant carrying sponge (Laid-open Japanese Patent No. 116360/1985) which consists of a spongy cellular mass and a liquid deodorant impregnated in it, and a process (Laid-open Japanese Patent No. 103518/1986) of manufacturing a deodorization filter comprising impregnating emulsion-type adhesive, powdered active carbon and a solid acid insoluble in water into cell membrane-free urethane foam and then drying. These are disadvantageous in the following: (1) allowing deodorant easily to come off the surface of the foam; (2) small water-and solvent-proofness, (3) limited carrying capacity, and (4) necessary redrying of the spongy cellular mass, reflected in complicated processing.

Additionally a deodorant composition is described in laid-open Japanese Patent 145143/1985. The composition contains an iron compound, ethylenediaminetetraacetic acid and alum together with blowing agent which are mixed when urethane foam, polystyrene foam resin, or the like is manufactured. This overcomes the defects involved in the above-mentioned compositions but proved that foaming of the resin is suppressed by an added deodorant composition, resulting in destruction of the cellular structure of the foam and inadequate deodorant power.

OBJECTS AND SUMMARY OF THE INVENTION

Under these circumstances, an object of the present invention is to provide a deodorant suitable to be contained in urethane foam.

An another object is to provide a deodorant carrying urethane foam having a superior deodorant power and good properties containing a deodorant having a specified constitution or composition.

A further object is to provide a process of preparing such deodorant carrying urethane foams as stated in the previous objects.

As the results of concentrated endeavor by the inventors for achieving the above-mentioned objects, the invention has been accomplished on the basis of the knowledge that a deodorant carrying urethane foam having powerful deodorant characteristic and good in other properties could be obtained by the use of a deodorant having a specified composition.

The invention provides a deodorant carrying urethane foam characterized in that chemically-reactive deodorant is distributed uniformly in the cellular mass of a urethane foam, and when kept at atmospheric pressure and 150° C. for one hour, weight loss of the deodorant should be not more than 15%.

Such deodorant carrying urethane foam is prepared by the process comprising adding a chemically-reactive deodorant having a characteristic of resulting in weight loss of not more than 15% when kept at atmospheric pressure and 150° C. for one hour to the composition of an intended urethane foam to allow the deodorant to be distributed uniformly in the composition, and then subjecting the resultant mixture to foaming.

Suitable deodorants for use in the present invention are essential to be the so-called chemically-reactive substances capable of deodorizing stably undesirable substances by addition, condensation or neutralization, or converting them into odorless substances by oxidation or reduction, or substituting them with odorless substances by ion exchanging reaction. On the other hand, physical adsorptive deodorant such as activated carbon, and biological deodorant such as enzyme are not adequate because of their sharp reduction of activity with time when in use. Chemically-reactive deodorants which do not meet the condition that weight loss of them should be not more than 15% when kept at atmospheric pressure and 150° C. for 1 hour are not suitable, too. Besides it is favorable from the standpoint of quality of the deodorant urethane form that change of color could not be caused by such heating.

Suitable examples of chemically-reactive deodorant for use in the present invention are anhydrous metal sulfates such as iron sulfate, copper sulfate, zinc sulfate, aluminum sulfate; anhydrides of metal nitrates such as copper nitrate and zinc nitrate; phosphoric acids, such as metha-phosphoric acid, pyrophosphoric acid, tripolyphosphoric acid, and acid salts thereof; polycarboxylic acids having 4 or more carbon atoms such as tartaric acid and fumaric acid, and metal salts thereof; monocarboxylic acids having 8 or more carbon atoms such as oleic acid, naphthenic acid and stearic acid, and metal salts thereof; and $\alpha, \beta$-unsaturated dicarboxylic anhydride polymers.

These deodorants may be used alone, in combination of a plurality of them or any other form, as long as it meets the above-mentioned conditions. Besides combined use of them with active carbon and zeolite may be allowed as long as their deodorant powers are not impaired.

The hydrates of the above-mentioned inorganic salts may be used in combination with the above-mentioned chemically-reactive deodorants as long as they meet the condition that the weight loss is not more than 15% under the above-stated condition.

In the present invention, the term "$\alpha, \beta$-unsaturated dicarboxylic anhydride polymer" denotes a polymer or copolymer of $\alpha, \beta$-unsaturated dicarboxylic anhydride, and includes those in which a part of the unit of the $\alpha, \beta$-unsaturated dicarboxylic anhydride is converted into a carboxylic group by a known reaction such as hydrolysis or alcoholysis.

Examples of $\alpha, \beta$-unsaturated dicarboxylic anhydrides for use in the present invention are maleic anhydride, itaconic anhydride, and citraconic anhydride, and particularly maleic anhydride is favorable from the viewpoint of reactivity and economy.

Examples of monomers copolymerizable with $\alpha, \beta$-unsaturated dicarboxylic anhydrides are aromatic monoolefins such as styrene, $\alpha$-methylstyrene and vinyltoluene; and aliphatic monoolefins such as ethylene, propylene, isobutene, butene-1, butene-2, pentene-1, pentene-2, 2-methylbutene-1, 2-methylbutene-2, hexene-1, 2,2,4-trimethylpentene-1, 2,2,4-trimethylpentene-2, decene-1, octadecene-1; cyclic monoolefins such as cyclopentene, cyclohexene and cyclooctene; aliphatic diolefins such as butadiene, isoprene and piperylene; cyclodiolefins such as cyclopentadiene; unsaturated carboxylic acids such as acrylic acid and methacrylic acid; unsaturated carboxylic acid esters such as ethyl acrylate and methyl methacrylate; unsaturated nitriles, such as acrylonitrile, methacrylonitrile; vinyl halogenides such as vinyl chloride; vinyl carboxylates such as vinyl acetate; vinyl ethers and such as methyl vinyl ether; unsaturated sulfonic acids such as vinylsulfonic acid and p-styrenesulfonic acid.

Methods for obtaining $\alpha, \beta$-unsaturated dicarboxylic anhydride polymers are not in particular limited but known techniques, for example, emulsion polymerization and solution polymerization can be used.

The amount of units derived from $\alpha, \beta$-unsaturated dicarboxylic anhydrides contained in an $\alpha, \beta$-unsaturated dicarboxylic anhydride polymer is not limited in particular, and is usually 1 or more mol %, preferably 5 mol % or more in relation to all monomer units constituting the $\alpha, \beta$-unsaturated dicarboxylic anhydride polymer. Too low a content of this reflects in too high added amount of deodorant component in relation to the urethane foam mass, which presents a problem to the cellular structure of the urethane foam.

Molecular weights of $\alpha, \beta$-unsaturated dicarboxylic anhydrides are not limited in particular, and usually are between 500 to 500,000, preferably 1,000 to 300,000.

The deodorant carrying urethane foam is prepared, principally in the same way as the prior art for foamed material, by mixing an isocyanate compound, a compound having active hydrogen, and as desired, a cross-linking agent, a catalyst, a blowing agent and a surface active agent, and then causing the resultant mixture to react and produce a foam.

Isocyanate compounds as ingredients suitable for use in preparing urethane foam are not in particular limited, and the following are typical examples: diisocyanate compounds such as 4,4'-diphenylmethane diisocyanate (MDI), tolylenediisocyanate (TDI) and hexamethylene diisocyanate (HMDI), and mixtures thereof Polyisocyanates produced by causing these diisocyanates, as with glycol or triol, to remain as unreacted isocyanate groups at the end may be used.

Compounds having active hydrogen suitable for use in combination with the above-mentioned isocyanate compounds are not limited in particular, and the following are typical examples: dihydric alcohols such as ethylene glycol, propylene glycol, 1,4-butanediol, 1,6-hexanediol, diethylene glycol and neopentyl glycol; tri- or more hydric alcohols such as glycerin, trimethlolpropane, pentaerythritol, sorbitol, methyleneglucoside and sucrose; polyhydric phenols such as pyrogallol and hydroquinone; aliphatic polycarboxylic acids such as succinic acid and adipic acid; aromatic polycarboxylic acids such as phthalic acid, terephthalic acid, trimellitic acid; amines such as ammonia, alkylamines, alkylendiamines; and mixture thereof. Polyesterpolyols produced by causing reactions between the various alcohols and the various carboxylic acids may be used. Besides polyetherpolyols resulting from reactions between the various alcohols or phenols and ethylene or propylene oxides may be used.

Blowing agents suitable for use in producing foams in such as above-mentioned are water and/or halogen-substituted aliphatic hydrocarbon blowing agents such as methylene chloride, and trichloromonofluoromethane.

Typical examples of cross-linking agents to be incorporated in such a mixture material as above-mentioned are low molecular polyols having tri- or higher valency such as glycerin, trimethylolpropane. triethanol amine, tetra (hydroxypropyl)ethylene diamine.

Typical examples of catalysts suitable for use in the present invention are: tertiary amines such as N,N-dimethylethanol amine and ethylmorpholine; organic tin compounds such as tin octenate and dibutyltin diacetate; organic lead compounds such as lead octenate; or calcium carbonate.

Moreover in preparing urethane foam having special properties other additives or materials such as pigment, antioxidant, ultraviolet absorber, fire-retardant, antifungal agent and solvent may be used.

In preparing deodorant carrying urethane foam according to the inventio, too small of an amount of deodorant incorporated in the above-mentioned urethane foam composition results in an inadequate deodorant power of the foam. In general the deodorant power becomes greater with increasing amounts of deodorant. Too large of an amount of deodorant added may cause the physical properties of the obtained urethane foam to be impaired. Thus the normal amount of deodorant to be used is within the range of 0.05 to 20% by weight. The deodorant alone or concomitantly with other ingredients may be added in the urethane composition before or during foaming.

The deodorant carrying urethane foam according to the invention in which chemically-reactive deodorant having the specified characteristic is uniformly distributed, as above-described, has advantages: it can be used without allowing the deodorant power to decrease and to come off the urethane foam; and is superior in waterproofness, easily manufacturable and highly economic.

DESCRIPTION OF THE PREFERRED EMBODIMENTS

An embodiment of the invention will be described in detail by way of examples together with citations for comparison and reference, in which parts and % are expressed by weight unless otherwise specified.

EXPERIMENT 1

Seven deodorants shown in Table 1 were sampled. Each sample (1 g) was weighed on an aluminium dish, and kept at 150° C. in a hot-air circulation oven for one hour. Then the weight loss was measured and the obtained results were summarized in Table 1.

TABLE 1

| Sample No. | Deodorant | Wt. loss (%) 150° C., 1 hr | Form sp. gr. Foamed state | $NH_3$-deodorz. (%) at 1 hr |
| --- | --- | --- | --- | --- |
| (1) | Acid sodium pyrophosphate | 0.6 | 0.030 Good | 100 |
| (2) | Acid sodium pyrophosphate + $Cu_2SO_4.5H_2O$ *1 | 3.1 | 0.030 Good | 100 |
| (3) | Styrene/maleic anhydride copolymer *2 | 8.4 | 0.030 Good | 100 |
| (4) | Styrene/maleic anhydride copolymer + copper | 9.1 | 0.030 Good | 100 |

TABLE 1-continued

| Sample No. | Deodorant | Wt. loss (%) 150° C., 1 hr | Form sp. gr. Foamed state | $NH_3$-deodorz. (%) at 1 hr |
|---|---|---|---|---|
| | oleate *2, *3 | | | |
| (5) | Citric acid | 19.2 | 0.037 Light brown | 46 |
| (6) | $Fe_2SO_4.7H_2O$/ Ascorbic acid *4 | 34.9 | *6 | Not tested |
| (7) | $Fe_2SO_4.7H_2O$/ Alum/EDTA *5 | 30.5 | 0.048 Brown | 53 |
| (8) | Not added | — | 0.030 | 27 |

*1 Copper sulfate pentahydrate (one part by weight) was added to acid sodium pyrophosphate (100 parts by weight).
*2 mol ratio: 50/50, MW = 1000
*3 Copper oleate (one part by weight) was added to the copolymer (100 parts by weight).
*4 L-ascorbic acid (one part by weight) was added to ferrous sulfate heptahydrate (100 Parts by weight).
*5 Ferrous sulfate.7H2O/burnt alum/EDTA = 1:3:0.03 (by weight)
*6 Forming rate is low and unhardened, and get brown.
Sample Nos. (5), (6), (7) and (8) are presented for comparison.

EXPERIMENT 2

First, a polyol (100 parts; GR3000, Sanyo Chemicals Co., Ltd.) was mixed with a deodorant (2 parts) to form mixture A On the other hand, TDI-80 (NCO Index: 105), which is a mixture of 2,4-TDI 80% and 2,6-TDI 20% (42 parts), water (3.2 parts), tin octenate (0.3 parts), triethylene diamine (0.2 parts) and silicon oil (1.5 parts) were mixed. The latter mixture is called mixture B. The former mixture A and the mixture B were mixed in a mixer to cause reaction between them and production of a foam. Thus deodorant carrying urethane foams (1) to (7) and a deodorant-free urethane foam (8) in Table 1 were obtained. The specific gravity of the deodorant-free urethane foam (8) was set to 0.03. Of the deodorant carrying urethane foams (1) through (7), the formed cellular structures were observed and the specific gravities were measured. Each obtained urethane foam (1 g) was weighted, transferred to a 500 ml-Erlenmeyer flask air-filled and containing 0.7 mg of ammonia, and tightly stoppered. The change in ammonia concentration of the gaseous phase was measured by gas chromatography and the deodorization rate was calculated out. The obtained results are given in Table 1.

EXPERIMENT 3

Urethane foams (2), (3) and (8) obtained in Example 1 were sampled. A sample (1 g) was weighed, placed a 500 ml-Erlenmeyer flask air-filled and containing methyl mercaptan (0.1 mg), and tightly stoppered. The change in methyl mercaptan concentration of the gas phase was measured by gas chromatography. The obtained results are given in Table 2.

TABLE 2

| Sample No. | Deodorant | $CH_3SH$-deodorization rate (%) at 24 hrs |
|---|---|---|
| (2) | Acid sodium pyrophosphate + $Cu_2SO_4.5H_2O$ *1 | 98 |
| (4) | Styrene/maleic anhydride copolymer + Copper oleate *2 | 100 |
| (8) | Not added | 43 |

*1 Copper sulfate pentanhydrate (one part by weight) was added to acid sodium pyrophosphate (100 parts by weight).
*2 mol ratio: 50/50, MW = 1000
Sample No. (8) is presented for comparison.

EXPERIMENT 4

The urethane foam (1) obtained in Example 1 was immersed in water for 1 hr, and dried. The ammonia removal power was measured in the same way as in Example 1. In addition, acid sodium pyrophosphate powder (100 parts) was mixed with a 1% aqueous carboxymethyl cellulose solution (200 parts) uniformly therein. It was impregnated into a urethane foam prepared without adding any deodorant (No. 8), and dried at 120° C. for 1 hr. Thus was obtained a deodorant carrying urethane foam (Sample No. 9) containing as a deodorant sodium pyrophosphate in 2%. The similarly-yielded results of this comparative sample are given in Table 3.

TABLE 3

| Sample No. | Deodorant | Removal (%) at 1 hr | |
|---|---|---|---|
| | | Bef. Imm. | Aft. Imm. |
| (1) | Acid sodium pyrophosphate | 100 | 100 |
| (9) | Acid sodium pyrophosphate (impregnation) | 100 | 27 |

Sample No. (9) is presented for comparison.

The results above-mentioned have demonstrated that the deodorant carrying urethane form according to the invention has appropriate foam structure, good deodorant power, and thus high quality.

What is claimed is:

1. A deodorant-carrying urethane foam having a deodorant power superior to that of a urethane foam produced by an impregnation process, said deodorant-carrying urethane foam being produced by a process comprising the steps of (a) uniformly dispersing a chemically-reactive deodorant in a stock mixture from which a urethane foam is produced, said chemically-reactive deodorant being added in an amount of 0.05-20% by weight with respect to the stock mixture, said chemically-reactive deodorant being selected from the group consisting of anhydrous sulfates, anhydrous nitrates, phosphoric acids and acid salts thereof, anhydrous polycarboxylic acids having 4 or more carbon atoms and metal salts thereof, α, β-unsaturated dicarboxylic anhydride polymers, and mixtures thereof, said deodorant exhibiting a weight loss of not more than 15% when maintained at 150° C. under atmospheric pressure for one hour; and (b) foaming said stock mixture.

2. A deodorant-carrying urethane foam as defined in claim 1, wherein said α, β-unsaturated dicarboxylic anhydride polymers are styrene/maleic anhydride copolymers.

3. A deodorant-carrying urethane foam as defined in claim 1, wherein said chemically-reactive deodorant consists of a mixture of an acid phosphate and an anhydrous sulfate or anhydrous nitrate.

4. A deodorant-carrying urethane foam as defined in claim 1, wherein said chemically-reactive deodorant consists of a mixture of an acid pyrophosphate and anhydrous copper sulfate.

5. A deodorant-carrying urethane foam as defined in claim 1, wherein said chemically-reactive deodorant consists of a mixture of an α, β-unsaturated dicarboxylic anhydride polymer and (b) at least one compound selected from anhydrous polycarboxylic acids having 4 or more carbon atoms and metal salts thereof, and anhydrous monocarboxylic acids having 8 or more carbon atoms and metal salts thereof.

6. A deodorant-carrying urethane foam as defined in claim 1, wherein said chemically-reactive deodorant consists of a mixture of a styrene/maleic anhydride copolymer and copper oleate.

7. A deodorant-carrying urethane foam as defined in claim 1, wherein said acid salts of phosphoric acids comprise acid pyrophosphate.

8. A deodorant-carrying urethane foam as defined in claim 1, wherein the stock mixture comprises an isocyanate compound and a compound having active hydrogen.

9. A deodorant-carrying urethane foam having a deodorant power superior to that of a urethane foam produced by an impregnation process, said deodorant-carrying urethane foam being produced by a process wherein (a) a chemically-reactive deodorant is dispersed in at least one component of a stock mixture from which a urethane foam is produced, said chemically reactive deodorant being added in an amount of 0.05 to 20% by weight with respect to the stock mixture, said chemically-reactive deodorant being selected from the group consisting of anhydrous sulfates, anhydrous nitrates, phosphoric acids and acid salts thereof, anhydrous polycarboxylic acids having 4 or more carbon atoms and metal salts thereof, anhydrous monocarboxylic acids having 8 or more carbon atoms and metal salts thereof, $\alpha, \beta$-unsaturated dicarboxylic anhydride polymers, and mixtures thereof, said deodorant exhibiting a weight loss of not more than 15% when maintained at 150° C. under atmospheric pressure for one hour; and (b) foaming said stock mixture.

10. A deodorant-carrying urethane foam as defined in claim 9, wherein the components of the stock mixture include an isocyanate compound, a compound having active hydrogen and a blowing agent.

* * * * *